(12) United States Patent
Xu et al.

(10) Patent No.: US 8,346,329 B2
(45) Date of Patent: Jan. 1, 2013

(54) APPARATUS AND METHOD FOR NONINVASIVE HUMAN COMPONENT MEASUREMENT WITH SELECTABLE OPTICAL LENGTH

(75) Inventors: Kexin Xu, Tianjin Province (CN); Zhenhui Du, Tianjin Province (CN)

(73) Assignee: Tianjin Sunshine Optics Technologies Co., Ltd., Tianjin (CN)

( * ) Notice: Subject to any disclaimer, the term of this patent is extended or adjusted under 35 U.S.C. 154(b) by 1393 days.

(21) Appl. No.: 12/007,427

(22) Filed: Jan. 10, 2008

(65) Prior Publication Data

US 2008/0171925 A1 Jul. 17, 2008

(30) Foreign Application Priority Data

Jan. 12, 2007 (CN) .......................... 2007 1 0056441

(51) Int. Cl.
*A61B 5/1455* (2006.01)
(52) U.S. Cl. .................. 600/316; 600/310; 600/322
(58) Field of Classification Search .................. 600/310, 600/316, 322, 340, 473, 476; 356/479, 497
See application file for complete search history.

(56) References Cited

U.S. PATENT DOCUMENTS

| 4,169,676 | A | 10/1979 | Kaiser |
| 4,655,225 | A | 4/1987 | Dähne et al. |
| 5,795,295 | A * | 8/1998 | Hellmuth et al. ............. 600/310 |
| 6,611,338 | B1 * | 8/2003 | Knuttel et al. ................ 356/479 |
| 2005/0057756 | A1 * | 3/2005 | Fang-Yen et al. ............. 356/497 |
| 2005/0190372 | A1 * | 9/2005 | Dogariu ........................ 356/479 |
| 2009/0011038 | A1 | 1/2009 | Seiler et al. |

FOREIGN PATENT DOCUMENTS

| JP | 6-63049 | 3/1994 |
| JP | 9299333 A | 11/1997 |
| JP | 10-332329 | 12/1998 |
| JP | 11-188007 | 7/1999 |
| JP | 11-239567 | 9/1999 |
| JP | 2002-82045 | 2/2002 |
| JP | 2003-121347 | 4/2003 |
| JP | 2006-70881 | 3/2006 |
| JP | 2006-320380 | 11/2006 |

(Continued)

OTHER PUBLICATIONS

Yunhan Luo et al., "Analysis of sensitivity and optical path-length in non-invasive measurement of glucose with near infrared spectroscopy", Proc. SPIE 5696, 205 (2005).*

(Continued)

*Primary Examiner* — Eric Winakur
*Assistant Examiner* — Chu Chuan (JJ) Liu
(74) *Attorney, Agent, or Firm* — Jacobson Holman PLLC

(57) ABSTRACT

A method and apparatus for noninvasive measurement of a human body component, such as glucose, in vivo, include near infrared spectroscopy based laser sources driven at a carrier frequency lying within the characteristic absorption of the component. The apparatus also drives the laser diodes with a modulation frequency to generate a frequency difference between the measuring light and reference beam, and the interference of the two beams results in a beat frequency signal, which frequency is proportional to the optical path difference between the measuring light and the reference beam. The scattering lights from human tissue with different optical lengths are simultaneously detected and selected based on the beat frequency. The method is a convenient embodiment of the floating reference principle, which takes advantage of optical length selection.

8 Claims, 3 Drawing Sheets

FOREIGN PATENT DOCUMENTS

| | | |
|---|---|---|
| JP | 2007-005101 | 1/2007 |
| JP | 2007-159320 | 6/2007 |
| JP | 2009-512722 | 3/2009 |

OTHER PUBLICATIONS

Takeaki Yoshimura, "Tomographic Measurements by Optical Frequency Domain Reflectometry." The Japan Society for Precision Engineering, vol. 64, No. 9, 1998 (Abstract).

Ichirou Yamaguchi "Recent Progress in Optical Interferometry" (Abstract) pp. 641-647, 2000.

Takeaki Yoshimura "Optical coherence tomography in scattering media using a frequency-modulated tunable LCD source." (Abstract) pp. 655-658, 2000.

Takeaki Yoshimura. "Light Scattering Tomography" (Abstract) vol. 64, No. 9, pp. 1274-1278 (1998).

* cited by examiner

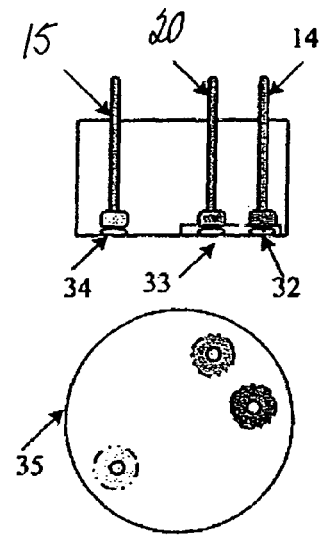
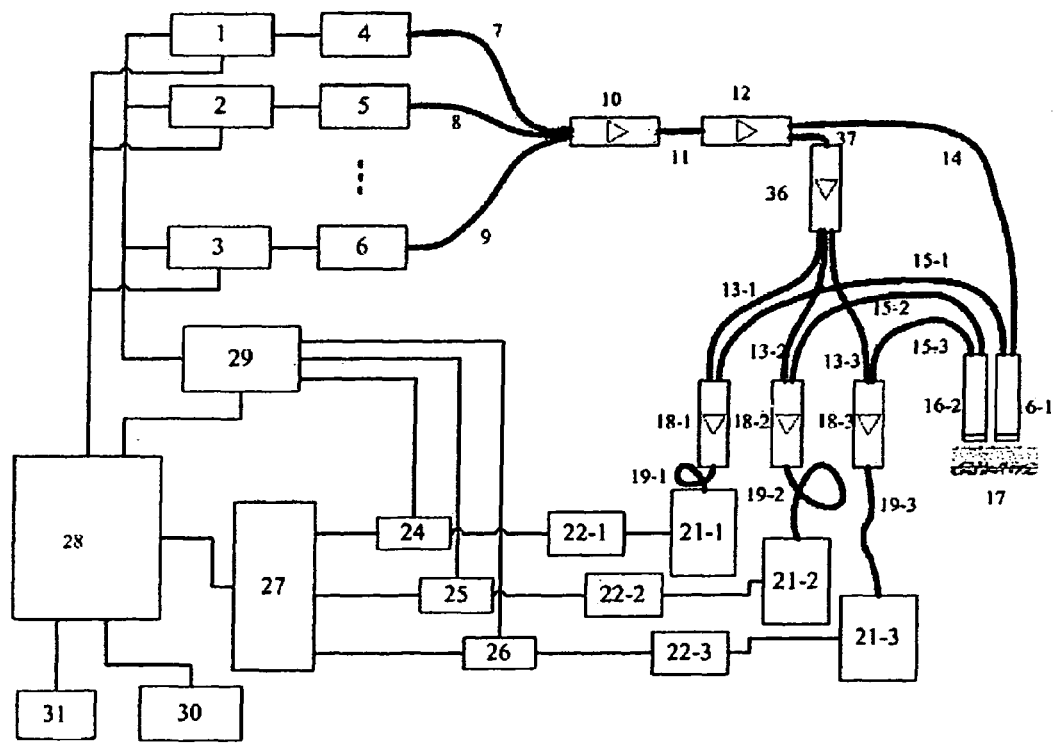
Fig. 5
Fig. 6

APPARATUS AND METHOD FOR NONINVASIVE HUMAN COMPONENT MEASUREMENT WITH SELECTABLE OPTICAL LENGTH

FIELD OF THE INVENTION

This invention relates to the method and apparatus to detect human component noninvasive. Particularly, this invention relates to the use of modulated tunable diode lasers (TDLs) in order to improve the measuring accuracy of noninvasive determining the concentration of the human component, such as glucose, in vivo.

BACKGROUND

The component in human body is the significant information for evaluating human health condition and is also the crucial standard for medical diagnose. The component is very low contents in the human body. The current testing method is to obtain the blood sample from finger tip, earlobe or vein, then use one-off reagent to handle chemical testing. This kind of invasive measurement is very complicate, painful and has the risk of infection. It restricts the on time and frequent measurement, and hampers the proper healthy treatment and management. In this respect, noninvasive human blood composition testing is of significant meaning in the treatment of disease and also in the research of disease.

Among every component of the human blood, glucose concentration is the most focused subject. Glucose concentration is the most effective index for diabetic diagnose and treatment. Diabetic is a kind of metabolic disturbance which is caused by the abnormal component of glucose, and also can result in some kind of severe complicating disease such as diabetic ketoacidosis, cardiovascular disease, renal failure, ablepsia, acrogenic gangrene and infection. Diabetic is now becoming one of the biggest threat to human health.

Kaiser [U.S. Pat. No. 4,169,676, Oct. 2, 1979] is the first one who uses optical method to test human component. Dähne [U.S. Pat. No. 4,655,225, Apr. 7, 1987] proposed to use dispersive near-infrared Spectrophotometers in the human component test. Today, the methods of human component measurement are mainly concerned of the following ways: polarization method, Raman spectrology, light scattering coefficient method, opto-acoustic spectral method, mid-infrared spectrology, near-infrared spectrology, optical Coherence Tomography (OCT), and so on. Polarization method's testing position is the eyeball which is difficult for the patient to accept; and the oculogyration may change the optical path and enlarge the testing mistake; and several components within the eyeball will disturb the polarization and the double refraction will interfere and reduce the transition light intensity; and the deflection angle of glucose solution too small to detect. The difficulty of Raman spectrum method is that the absorption and scattering signal in biological tissue are very weak and the background fluorescence interference comes from protein molecule is very powerful. Opto-acoustic spectrum method is too sensitive to the change of tissue structure and mid-infrared spectrum method is not very good at penetrating the tissue deeply enough.

The near infrared absorption, which wavelength range is 780 nm-2500 nm, is mainly caused by frequency doubling of the molecular vibration or combination frequency of several compounds which have the chemical bond X—H, such as C—H, and O—H, and N-H. Based on the characteristic absorption spectrum, the ingredient contents can be tested, and glucose can be done also. Recently, the progress of computer and chemometrics technology enhance the sensitivity, precision, accuracy and reliability of quantative analysis dramatically, near infrared spectroscopy widely used in some crucial area such as pharmacy, agriculture and petroleum. Compared with middle infrared wavelength area, the detector has much higher sensitivity and response speed, the radiant efficiency of the light source is higher, its optical elements are more reliable, costless, and have less effect from the outside working environment. Little or no need for sample preparation so that it is suit for rapid field test and real-time analysis. Near infrared spectrum method has the merits of high-speed, nondestructive, high efficiency and also has high penetrating ability of human sap and parenchyma, therefore it is the proper test wavelength area for the measurement. A successful example is the success of noninvasive measuring of human blood oxygen saturation degree using near infrared light.

The key obstacles which reduce the accuracy of noninvasive near-infrared human components test lie in the following:

(1) The signal is always very weak because of the huge amount of water in tissue which absorbs light in near infrared region very effective. And the glucose concentration in the blood is low, which less than 0.1%, and its absorption in near infrared region is very weak. To detect the components in vivo requires the instrument with very high Signal-to-Noise ratio (SNR).

(2) Variety of measuring condition: The variety of testing condition such as testing position, and borne pressure, and the area of incident light, will greatly change the optical path of light transport in the tissue. And the signal caused by this change is much more significant than that caused by the variety of glucose concentration. It is difficult to immobilize this change condition or eliminate them, to obtain the useful signal.

(3) Variety of human physiological statue: The variety of human physiological statue changes the signal greatly, which is much bigger than that caused by concentration variety of the components. So, it results in the overwhelming of the useful signal for determining the concentration of the human component.

The signal is the multi-result of blood component and optical character of the skin. Many components of human body have absorption in near infrared spectrum, at the mean time, these spectrum are often over overlapping. The light transportation process is very complicate and has lots of optical path between the emission and reception. As shown in FIG. 2, there is big randomness of optical length. In direct receiving light scheme, all of this optical path which has experienced lots of the absorption and scattering of the human tissue coming into the photoelectric detector and cause the high complexity of the signal.

SUMMARY OF THE INVENTION

In order to overcome all these difficulties and get a solution of the overlapping spectrum, high complexity and low particularity of the signal, the object of this invention is to provide a method and apparatus for noninvasive human components measurement using near infrared spectroscopy with a selectable optical length. By measuring the absorption spectrum from certain position on human body and certain testing of particular optical length, this noninvasive, real-time, high speed human body composition measurement can be achieved.

The technical scheme of the invention is in: a method for noninvasive human component measurement with a selectable optical length, which performs the human component measurement by detecting a laser transportation in human tissue and is characterized in that: said laser is modulated, based on an interference between measuring beam and reference beam, the interference's beat frequency is proportional to an optical length difference between the measurement light and the reference light, and by selecting a certain reference optical length and using a phase sensitive detector circuit to process the beat frequency signal, a single optical length is selected from those human tissue scattering light so as to apply the measurement to a certain depth and part of the tissue.

Preferably, said step of selecting a signal optical length from those human tissue scattering light consists of either adopting a single detector or a single light source, or adopting a plurality of detectors or a plurality of light sources; and irradiating the light to a large area or receiving the scattering from a large area.

Preferably, the scattering light from human tissue with different optical lengths are simultaneously detected, and selecting at least one of the measuring optical lengths fitting the floating reference principle, which is the zero or rear zero sensitivity, used as the reference value; and selecting another one that fitting the floating reference principle, which is the maximum sensitivity, used as the measuring value for calculation the concentration of the component in the body.

Preferably, the beat frequency signals are selectively received according to their frequency; so as to select the different optical lengths propagating in the tissue, filter out the interferences from other light beams with different optical lengths.

Preferably, the optical length of the selected scattering light is changed by using the frequency selecting method, so as to be adaptable to the difference among floating point, i.e., the reference point and measurement point, due to different human body characteristics.

The technical scheme of the invention is also in: an apparatus for noninvasive human component measurement with a selectable optical length, which include a light driving controller, a light source, an interference light path, a signal conditioning circuit, a probe, a modulation signal generator and a micro computer, and is characterized in that: said light source is formed by a plurality of laser diodes; the signal conditioning circuit is formed by a preamplifier, a phase locking amplifier and an A/D converter; and a signal outputted from the A/D converter is inputted into the micro computer.

Preferably, the laser used in the measurement has a near infrared wavelength of 800 nm to 2500 nm which includes the frequency doubling vibration and combination frequency vibration of glucose molecule.

OBJECTS OR ADVANTAGES OF THE PRESENT INVENTION

The invention is based on the interference between measuring beam and reference beam, where the beat frequency is proportional to the optical length difference between measuring beam and reference beam. By selecting certain reference optical length and using phase sensitive detector circuit to process beat frequency signal, the single optical length is selected from human tissue scattering light. In the respect of single optical length reception, the enhancement of detector area or multiple detectors can result in the increase of light intensity so as to enhance the SNR.

In addition, this invention measure plural number optical length of the scattering light simultaneously. One of these is fit for the floating wavelength principle so as to build a realization of floating wavelength measurement method. Use modulation, filtering, pre-processing of the spectrum to realize the noninvasive, real-time and quickly human body component measurement. Therefore, this invention is convenient and has very high reliability of the testing result.

BRIEF DESCRIPTION OF THE DRAWINGS

FIG. 5 is the drawing of the probe.

FIG. 6 is the structure drawing of Embodiment 2.

| Reference Signs | |
| --- | --- |
| 1, 2, 3 | diode laser control drivers |
| 4, 5, 6 | laser diodes |
| 7, 8, 9, 11, | optical fibers |
| 13, 13-1, 13-2, 13-3, | optical fibers |
| 14, 15, 15-1, 15-2, 15-3, | optical fibers |
| 19, 19-1, 19-2, 19-3, | optical fibers |
| 20, 37 | optical fibers |
| 10, 12, | optical fiber couplers |
| 18, 18-1, 18-2, 18-3, 36 | optical fiber coupler |
| 16, 16-1, 16-2 | probes |
| 17 | part of tissue to be tested |
| 21, 21-1, 21-2, 21-3 | balanced photoelectric receivers |
| 22, 22-1, 22-2, 22-3 | preamplifiers |
| 23, 24, 25, 26 | phase locking amplifiers |
| 27 | A/D converter |
| 28 | micro computer |
| 29 | modulation signal generator |
| 30 | display |
| 31 | keyboard |
| 32 | configuration of incidence laser path |
| 33 | configuration of reference light path |
| 34 | configuration of measuring light path |
| 35 | housing of the probe |

DETAILED DESCRIPTION OF PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modification within the spirit and scope of the invention will become apparent to those skilled in the art from this detailed description.

This invention is benefit of laser's coherence, directivity and high spectral intensity, uses several laser diodes with various wavelength operated in frequency or time division mode, and wavelength modulated; and tests certain area of human body based on interference laser spectrum; and amplifies all the frequency components simultaneously, and extracts at least one of the frequency components fitting the floating reference principle, which is the zero or near zero sensitivity, used as the reference value; and extracts at least one of the frequency components that fitting the floating reference principle, which is the maximum sensitivity, used as the measuring value; and calculates the concentration of human components using the reference value and measuring value with the micro computer.

The object of this invention is to provide a noninvasive, real-time and in-vivo method and apparatus for testing human components. In order to overcome these difficulties, such as spectrum overlapping, high complexity and low particularity of the signal, the invention is achieved through modulated diode laser realizing certain optical length spectroscopy fitting floating reference methods, and testing certain human body area.

The Principle of Floating Reference Method

Figure 1:
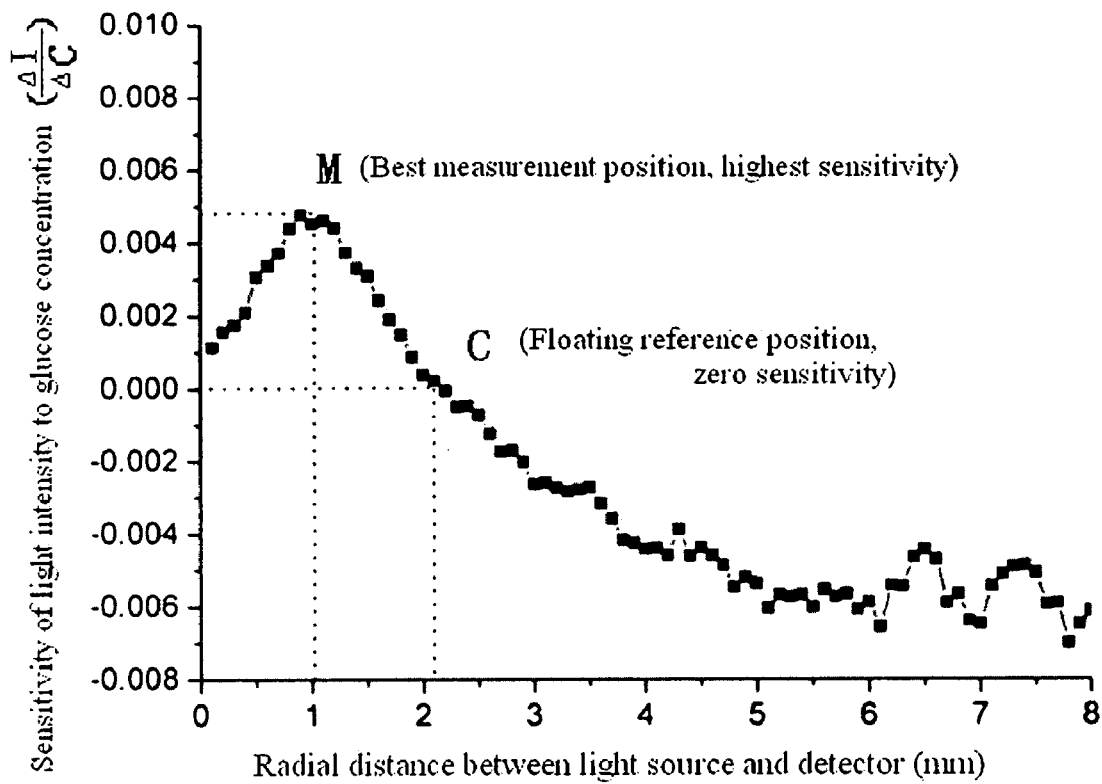
FIG. 1 shows the principle of floating reference measurement method.

When light transmit in the tissue, there exist a point M, called measurement point, where scattering light is the most sensitive to glucose concentration and a zero sensitive point C, called reference point, as shown in FIG. 1. The spectrum signal of reference point C contains the entire physiology changing which is irrelevant to glucose concentration. Measurement point M contains the largest amount signal of blood glucose concentration so that it is the best point for the testing. Measurement at these two point simultaneously and process difference afterward could reduce the interference of physiology changing significantly and enhance the precision and sensitivity of glucose concentration measurement.

Interference Modulating Laser Spectroscopy

Figure 3:
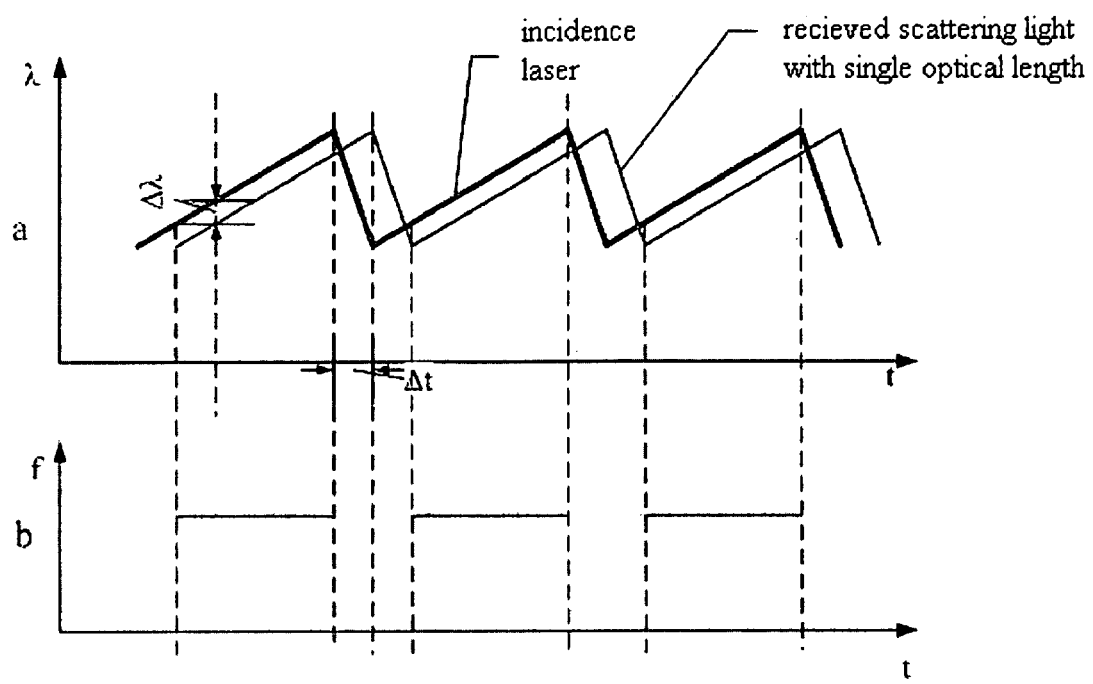
FIG. 3 shows the characteristic of the laser modulation and beat frequency signal.

Single optical length selection is based on the technology of interference modulating laser spectroscopy: The laser radiation, which is wavelength modulated so the wavelength changes with time (as shown in FIG. 3-$a$), is split into two beams, one is used as reference, called reference beam; and the other is for measuring, and called measuring beam. Measuring beam transmitted in optical fiber and collimated at the position that has plentiful arterial blood. Then the backward scattered light is collected and coupled into the fiber. It meets and interferers with the reference beam in fiber fused coupler. Because of the optical path difference between the two beams, the beat frequency of interference is given as:

$$f_d = \frac{\beta nL}{\lambda^2}$$

Where: $\lambda$ is the central wavelength of the laser;
$\beta$ is modulation factor of the laser diode; and
nL is the optical length of the measurement light (the testing fiber and reference fiber have the same length).

Figure 2:
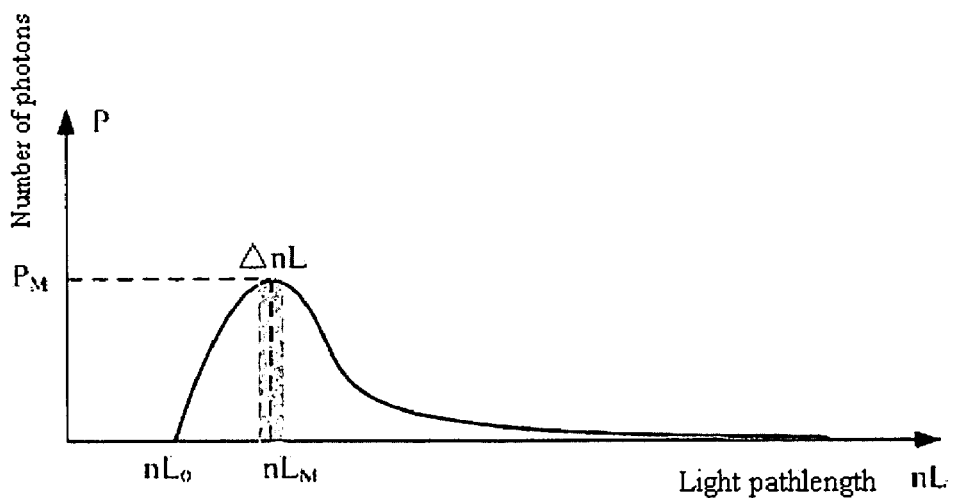
FIG. 2 shows the distribution of optical length between emission light and reception light.

The beat frequency of the interference is fixed for a single optical length, as shown in FIG. 3-$b$. As for the light scattered when transmitted in the body tissue, there are innumerable counts of optical length, so it is corresponding to innumerable counts of beat frequency, which obey the same distribution, as shown in FIG. 2. Thus, the scattering lights with different light paths in the tissue are converted into the beat frequency signals with different frequencies.

In addition, the detected beat frequency signal is amplitude modulated, converted from the wavelength modulated laser, and has the same frequency with the modulation frequency. The low frequency beat frequency signal is mainly about 1/f noise and fundamental wave equals to modulating frequency, 2$f$, 3$f$ are the harmonics of modulating frequency. The application of wavelength modulation spectroscopy is to transfer the DC signal to high frequency signal and can reduce various noise so as to improve the measuring SNR greatly.

Extracting Information of Certain Optical Length

Based on the technology of interference modulating laser spectroscopy mentioned above, the information of certain optical length can be extracted from selecting the interference beat frequency by using phase sensitive detector (PSD), as shown in FIG. 2. It can also filter the disturbing signal comes from other optical length, noise, and so on.

The information of different optical length of scattering light is obtained by adjusting the center frequency of PSD circuit; and the regulation of optical length range is obtained by setting the bandwidth of PSD circuit; and the information of multiple optical length is obtained by setting several signal channels, that is several PSD circuit with different central frequency, where each channel corresponds to different scattering optical length.

The technology of interference modulating laser spectroscopy profit from laser's coherence, directivity and high intensity, the laser radiation is focused onto the small point with plenty arterial blood of the body, so as to realize high spatial resolution. the indiscipline distribution of the light transportation, which scatters from protein, fat and muscle, is reduced benefit from single optical measurement of The technology of interference modulating laser spectroscopy, so as to reduce the signal randomicity and the spectrum's complexity which caused by the discrepancy of the tissue. The ration of certain optical characteristic and the concentration prediction of human component is realized.

The preferred embodiments of the invention will be illustrated with reference to the drawings below.

Figure 4:
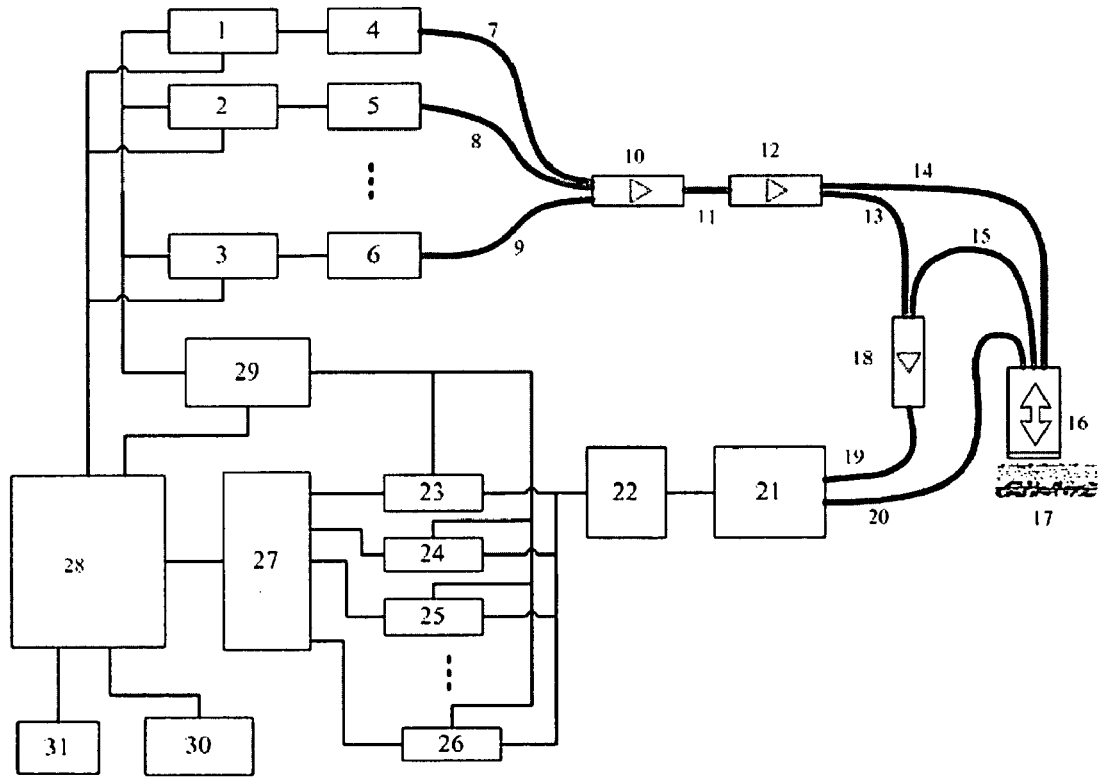
FIG. 4 is a diagram showing the system structure of Embodiment 1 and is also used for publication.

Embodiment 1:

Embodiment 1 of the invention is shown in FIG. 4, the system includes a laser driver controller 1, a laser driver controller 2, a laser driver controller 3, a laser source 4, a laser source 5, a laser source 6, an interference laser spectrum light path 7, an interference laser spectrum light path 8, an interference laser spectrum light path 9, an interference laser spectrum light path 10, an interference laser spectrum light path 11, an interference laser spectrum light path 12, an interference laser spectrum light path 13, an interference laser spectrum light path 14, an interference laser spectrum light path 15, an interference laser spectrum light path 18, an interference laser spectrum light path 20, a balanced photoelectric receiver 21, a signal processing circuit 22, a signal processing circuit 23, a signal processing circuit 24, a signal processing circuit 25, a signal processing circuit 26, a signal processing circuit 27, a micro computer 28, an optical probe 16, a modulation signal generator 29, a display 30 and a keyboard 31. This system is used to realize the interference laser spectrum technology and the multi-optical length separation technology.

The light source is near-infrared coherent source, which can use laser diode, gas laser, or dye laser. Several laser sources with different wavelength are used to cover the necessary wavelengths which needed for the components in human body. In the respect of glucose concentration measurement, we adopt several wavelength in the area of second order frequency doubling of glucose molecule (wavelength band from 1100 to 1300 nm), and first order frequency doubling area of glucose molecule (wavelength band from 1500 to 1800 nm), combination frequency area (wavelength band from 2100 to 2500 nm). In the embodiment, we adopt multiple laser diodes (three laser diodes are shown in the principle figure)

The laser driver controller (1, 2, 3) are used to control the output power of the diode laser, and to modulate the wavelength and to measure and control the temperature of diode laser.

Interference laser spectrum light path is comprised of a fiber 7, a fiber 8, a fiber 9, a fiber 11, a fiber 13, a fiber 14, a fiber 15, a fiber 19, a fiber 20, an optical fiber coupler 10, an optical fiber coupler 12, an optical fiber coupler 18, and a balanced photoelectric receiver 21. N numbers of lasers (three are shown in the figure) output the emitted laser into the fiber 7, the fiber 8, the fiber 9 and through the N×1 optical fiber coupler 10 (3×1 optical fiber coupler in the figure) into the fiber 11. The 1×2 optical fiber coupler 12 is used to separate the light into the measurement fiber 14 and the reference fiber 13; the laser that transmits in the measurement fiber 14 arrives at the optical probe, and through the incidence laser light path 32 (see FIG. 5), irradiates onto the skin tissue. The scattering light from deep skin tissue is collected by the measurement light path 34 (see FIG. 5) into the fiber 15, and is interfered with the reference light from fiber 13 in the optical fiber coupler 18. The interfered beam reaches the balanced photoelectric receiver 21 through the fiber 19. The reflection light from the surface of skin is collected by the reference light path 33 (see FIG. 5) and is then transmitted to the fiber 20 and then to the balanced photoelectric receiver 21 for reducing the laser source noise and other common-mode noise.

We set up several signal channel of demodulation circuit including a preamplifier 22, a phase locking amplifier 23, a phase locking amplifier 24, a phase locking amplifier 25, a phase locking amplifier 26, an A/D converter 27. The preamplifier 22 amplified the output signal from the balanced photoelectric receiver 21 and the signals from the preamplifier 22 contain absorption information of human component and transmit into several phase locking amplifiers (four are shown in FIG. 4), the output of the modulation signal generator 29 will also be sent into these phase locking amplifiers whose central frequencies are set differently to create several signal channels. Different signal channels correspond to different scattering light lengths. At least one reference value that satisfies the floating reference principle, which is the zero or near zero sensitivity, is selected as the reference value for calculation and another one that satisfies the floating reference measurement principle, which is the maximum sensitivity, is selected as the measurement value for calculation.

The entire output signal from phase locking amplifiers will be sent to the multi-channel AD converters 27 and thus be converted into a digital signal.

The micro computer 28, which can be embedded controller, PC, or signal chip processor, administrates the testing system through the peripheral circuits, which include the keyboard 31, the display 30, the laser driver controller 1, the laser driver controller 2, the laser driver controller 3, the modulation signal generator 29, and the multi-channel AD converter 27. The commands and necessary information is input through the keyboard. A display is used to show the operation information, which can be a digitron, a liquid crystal display (LCD), or a cathode ray tube (CRT). The micro computer 28 controls the temperature and current of the laser source 4, and the laser source 5, and the laser source 6 through the laser driver controller 1, the laser driver controller 2, the laser driver controller 3 respectively, and performs the modulation and output of the laser signal. The modulation signal generator 29 gives the characteristic parameters of the diode laser, which include modulation mode, and modulation factors, and modulation frequency. The multi-channel AD converter 27 outputs the signal into the micro computer 28 which performs digital signal processing including digital filtering, fault elimination, temperature compensation and background deduction and calculating the prediction value of human component according to the rating curve, and then the results are displayed on the display 30.

Explanation of the Probe

The proposal of the probe is shown in FIG. 5, including an incidence laser light path 32, a reference light path 33, a measurement light path 34 and a housing 35. A fiber 14, a fiber 20 and a fiber 15 are used to connect the probe with the interference laser spectrum light path. The light from the fiber 14 will be collimated with the incidence laser light path 32 and is pointed at the testing object. An optical stop is set up between the laser light path 32 and the measurement light path 34. The scattering light will be tested by the measurement light path 34 only if the light passes the deep tissue of the skin, and will then be coupled into the testing fiber 15. The reflection light from the skin will be collected by the reference light path 33 into the fiber 20.

Embodiment 2: the Application of a Plurality of Detectors

Embodiment 2 concerns a human component measurement system with a plurality of detectors as shown in FIG. 6. The 1×2 optical fiber coupler 12 is used to split the light beam into two beams. One of them passes a fiber 37 and then arrives at an optical fiber coupler 36 where the light is separated into three light paths as the reference lights to be transmitted through the fibers 13-1, 13-2, 13-3 to the optical fiber couplers 18-1, 18-2, 18-3. The other one passes a fiber 14 and arrives at a probe 16-1 to be transmitted through an incident laser light path 32 to irradiate the skin tissue. The measurement light collected by the probes 16-1 and 16-2 are transmitted to the optical fiber couplers 18-1, 18-2, 18-3 through fibers 15-1, 15-2, 15-3 so as to be interfered with the reference lights. The beat frequency signal will be received by photoelectric receivers 21-1, 21-2, 21-3 and amplified by preamplifiers 22-1, 22-2, 22-3. A phase locking amplifier 24, a phase locking amplifier 25, a phase locking amplifier 26 are used to select different optical lengths. An A-D converter 27 is used to perform the analog-digital conversion. A micro computer 28 is used to perform digital signal processing including digital filtering, fault elimination, temperature compensation and background deduction and calculating the prediction value of human component according to the rating curve, and then the results are displayed on the display 30.

The phase locking amplifier 24, the phase locking amplifier 25, and the phase locking amplifier 26 will be configured to obtain different frequencies so as to acquire several optical lengths to build several signal channels. At least one reference value that satisfies the floating reference measurement principle is selected as the reference value for calculation and another one that satisfies the floating reference measurement principle is selected as the measurement value for calculation.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of noninvasive measuring of a human component with a selectable optical length, the component being of a type that absorbs light at wavelengths within an absorption line range, the method comprising the steps of:

driving diode laser sources by laser drivers to provide wavelength modulated light;

splitting the wavelength modulated light into measuring light and reference light;

irradiating the measuring light to skin of a human body;

receiving scattering light from a tissue under the irradiated skin;

frequency selectively detecting beat frequency signals between the reference light and the scattering light by using a phase sensitive detector (PSD) circuit; and processing the detected beat frequency signals to determine a concentration of the component in the human body, wherein the scattering light from the human tissue having different optical lengths is simultaneously received and detected, a first scattering light having an optical length which is a zero or near zero sensitivity in compliance with a floating reference principle being selected, and a beat frequency signal between the reference light and the first scattering light being used as a reference value, and a second scattering light having an optical length which is a maximum sensitivity in compliance with the floating reference principle being selected, and a beat frequency signal between the reference light and the second scattering light being used as a measuring value for calculating the concentration of the component in the human body by referring to the reference value.

2. The method of claim 1, wherein at least one of the first scattering light and the second scattering light is selected either by adopting a single detector or a single light source, or by adopting a plurality of detectors or a plurality of light sources; and the measuring light beam is irradiated to a large area of the skin or the scattering light is received from a large area of the skin.

3. The method of claim 1, wherein the beat frequency signals are selectively detected according to their frequencies to select the first and the second scattering lights, so as to filter out interferences from other light having other optical lengths.

4. The method of claim 1, wherein the first and the second scattering lights are selected by using a frequency selecting method.

5. The method of claim 1, wherein the laser used in the measurement has a near infrared wavelength of 800 nm to 2500 nm which includes a frequency doubling vibration and combination frequency vibration of a molecule of the human component.

6. An apparatus for noninvasive human component measurement with a selectable optical length, the component being of a type that absorbs light at wavelengths within an absorption line range, the apparatus comprising:

diode laser sources configured to irradiate laser light of different wavelengths;

a modulation signal generator configured to generate modulation signals for modulating the laser light;

laser drivers configured to drive the diode laser sources with the modulation signals generated by the modulation signal generator to provide wavelength modulated light;

a first fused fiber coupler configured to split the wavelength modulated light into measuring light and reference light;

a probe configured to irradiate the measuring light to skin of a human body and to receive scattering light from a tissue under the irradiated skin;

a second fused fiber coupler configured to receive the reference light and the scattering light;

a signal conditioning circuit configured to frequency selectively detect beat frequency signals between the reference light and the scattering light by using a phase sensitive detector (PSD) circuit; and a micro computer configured to process the detected beat frequency signals to determine a concentration of the component in the human body, wherein the scattering light from the human tissue having different optical lengths is simultaneously received and detected, a first scattering light having an optical length which is a zero or near zero sensitivity in compliance with a floating reference principle being selected, and a beat frequency signal between the reference light and the first scattering light being used as a reference value, and a second scattering light having an optical length which is a maximum sensitivity in compliance with the floating reference principle being selected, and a beat frequency signal between the reference light and the second scattering light being used as a measuring value for calculating the concentration of the component in the human body by referring to the reference value.

7. The apparatus of claim 6, wherein the wavelength of the laser light irradiated by the laser diode sources and used in the measurement lies in a near infrared region of 800 nm to 2500 nm which includes a frequency doubling vibration and combination frequency vibration of a molecule of the human component.

8. The method according to claim 5, wherein the molecule is glucose.

* * * * *